United States Patent
Furusawa

(10) Patent No.: US 8,262,886 B2
(45) Date of Patent: Sep. 11, 2012

(54) APPARATUS FOR ANALYZING CHARACTERISTICS OF PARTICULATE WITH DIELECTROPHORESIS OF PARTICULATE BY APPLYING ANGLE-MODULATED WAVE AND METHOD FOR THE SAME

(75) Inventor: Hiroshi Furusawa, Kochi (JP)

(73) Assignee: Kochi University of Technology, Kami-Shi (JP)

( * ) Notice: Subject to any disclaimer, the term of this patent is extended or adjusted under 35 U.S.C. 154(b) by 1052 days.

(21) Appl. No.: 12/162,891

(22) PCT Filed: Jan. 30, 2007

(86) PCT No.: PCT/JP2007/051491
§ 371 (c)(1),
(2), (4) Date: Aug. 25, 2008

(87) PCT Pub. No.: WO2007/091450
PCT Pub. Date: Aug. 16, 2007

(65) Prior Publication Data
US 2010/0219075 A1     Sep. 2, 2010

(30) Foreign Application Priority Data

Feb. 10, 2006  (JP) ................................. 2006-034358

(51) Int. Cl.
*B01D 57/02*     (2006.01)
(52) U.S. Cl. .................... 204/547; 204/225; 204/643
(58) Field of Classification Search .................. 204/547, 204/643, 225
See application file for complete search history.

(56) References Cited

FOREIGN PATENT DOCUMENTS

| JP | 5137576 | 6/1993 |
|---|---|---|
| JP | 2001500252 T | 2/1998 |
| JP | 2002543972 T | 12/2002 |
| JP | 2003507739 T | 2/2003 |
| JP | 20030660004 | 3/2003 |
| JP | 2003107099 | 4/2003 |
| JP | 2004522452 T | 7/2004 |
| JP | 2005224171 | 8/2005 |
| JP | 2003000224 | 1/2007 |
| WO | WO 2004/055505 A1 | 7/2004 |

OTHER PUBLICATIONS

Bakewell, D.J et al., Jun. 2001, "Measuring the Frequency Dependent Polarizability of Colloidal Particles from Dielectrophoretic Collection Data," IEEE Transactions on Dielectrics and Electrical Insulation, 8(3):566-571.
Hakoda, M. et al., 2005, "Development of a Method to Analyze Single Cell Activity by Using Dielectrophoretic Levitation," Biotechnol. Prog, 21:1748-1753.
Lu, Yen-Sheng et al., 2006, "Controllability of non-contact cell manipulation by image dielectrophoresis (iDEP)," Optical and Quantum Electronics, 37:1385-1395.

*Primary Examiner* — J. Christopher Ball
(74) *Attorney, Agent, or Firm* — Law Offices of Albert Wai-Kit Chan, PLLC

(57) ABSTRACT

The present invention provides a method for analyzing characteristics of a particulate, comprising: selecting at least one particulate in a fluid; positioning said selected particulate in the vicinity of a pair of electrodes; applying a programmed voltage signal for generating a spatially inhomogeneous electric field between said pair of electrodes; detecting the movement of the particulate while applying said programmed voltage signal to create a time-series data corresponding to said movement of the particulate; and analyzing the characteristics of said particulate based on said time-series data.

40 Claims, 14 Drawing Sheets

APPARATUS FOR ANALYZING CHARACTERISTICS OF PARTICULATE WITH DIELECTROPHORESIS OF PARTICULATE BY APPLYING ANGLE-MODULATED WAVE AND METHOD FOR THE SAME

CROSS REFERENCE TO RELATED APPLICATION

This application is the National Stage of International Application No. PCT/JP2007/051491, filed Jan. 30, 2007, which claims priority of Japanese Application No. 2006-034358, filed Feb. 10, 2006, the entire disclosures of the preceding applications are incorporated by reference herein in its entirety.

FIELD OF THE INVENTION

This invention relates to a method for analyzing characteristics of a particulate and a measurement apparatus for the same. More specifically, the present invention aims at providing a method for analyzing characteristics of a particulate and an apparatus for the same, and it excels in easily and briefly optimizing an applied AC voltage frequency for the characteristics analysis on particulate characteristics (especially an electrical analysis) or for manipulation such as transfer, fractionation and concentration of the particulate with the dielectrophoretic force.

DESCRIPTION OF THE RELATED ART

With the recent development of biotechnology, various methods for manipulating a cell have been suggested. According to the cell manipulation method, in general, an inhomogeneous electric field is generated between electrodes in order to induce dielectrophoresis to the cell, and then the cell is transferred for any desired operations.

Japanese patent publication 5-137576 discloses one embodiment of such a cell manipulation. FIG. 13 shows the embodiment of the cell manipulation disclosed in Japanese patent publication 5-137576.

In the embodiment of the cell manipulation disclosed in Japanese patent publication 5-137576, first of all, a suspension layer (S) including a cell (C) is placed over a plate electrode (P). A needle electrode (N) is inserted into the surface of the suspension layer (S). The tip of the needle electrode (N) is covered with an insulating cover (I). An opening is formed on the tip of the insulating cover (I), so that the suspension flows inside the insulating cover (I) and contacts with the tip of the needle electrode (N).

While keeping the above-conditions, AC voltage is applied to both the plate electrode (P) and the needle electrode (N) in order to generate an inhomogeneous electric field between them. The inhomogeneous electric field generated between the plate electrode (P) and the needle electrode (N) polarizes the cell (C). Then, the cell (C) moves so as to make the electric field to be homogeneous.

Here, the moving direction of the cell (C) depends on the frequency of the applied AC voltage. The object of the cell manipulation disclosed in Japanese patent publication 5-137576 is to attach several cells (C) to the tip of the needle electrode (N), subsequently to apply a DC pulse voltage to the needle electrode (N) to fuse the several cells (C) adhered to the needle electrode (N). Thus, the frequency of the applied AC voltage needs to be determined such that the cells (C) are attracted toward the needle electrode (N).

Japanese patent publication 2001-500252 discloses an apparatus suitable for determining the frequency of the AC voltage at which the cells (C) are attracted toward the needle electrode (N). FIG. 14 shows a main part of the apparatus disclosed in Japanese patent publication 2001-500252.

The apparatus disclosed in Japanese patent publication 2001-500252 comprises a common electrode (M) and an electrode array (A). The electrode array (A) includes multiple conductors (a). The common electrode (M) and the electrode array (A) are placed in a chamber (not shown) receiving a suspension, and the suspension inside the chamber includes several types of cells.

The AC voltages of different frequencies are applied to the respective multiple conductors (a) in order to generate the electric fields with different frequencies between the tips of the respective conductors (a) and the common electrode (M). Then, according to the generated electric fields, a specific type of cells gathers to the tip of a specific conductor (a). By investigating the type of cells gathered in the tip of the specific conductor (a), the AC frequency for attracting the specific type of cells can be decided.

By combining the techniques disclosed in Japanese patent publication 5-137576 with Japanese patent publication 2001-500252, the manipulations for the cell fusion may be preferably carried out.

Next, conventional manipulations of the cell fractionation will be explained.

The above-mentioned apparatus disclosed in Japanese patent publication 2001-500252 mainly aims at fractionating cells. By applying the AC voltages of different frequencies to the respective conductor (a), the gathered cells to the respective conductor (a) are sorted by the types of the cells. Then, the cells gathered to the respective conductor (a) are collected to complete the manipulation of the cell fractionation.

Japanese patent publication 2004-522452 discloses other method for manipulating the cell fractionation. The method disclosed in Japanese patent publication 2004-522452 selectively stains the cell to be separated, provides different dielectrophoretic characteristics to the cell, and therefore the desired cell is separated or isolated.

Japanese patent publication 2003-66004 discloses other apparatus for manipulating the cell fractionation. The apparatus disclosed in Japanese patent publication 2003-66004 uses the balance between a dielectrophoretic force to microparticles and a flow force of a suspension including the microparticles in order to carry out the cell fractionation.

By using the balance between the dielectrophoretic force to the microparticles and other force disclosed in Japanese patent publication 2003-66004, a cell activity may be also measured.

Japanese patent publication 2005-224171 further provides a method for analyzing a dielectrophoretic activity in such a manner. According to Japanese patent publication 2005-224171, cell characteristics are varied by the cell activity. A different cell activity results in a different dielectrophoretic force to the cell. Therefore, some cells stays at a different position in a fluid from the other cells with different activity as a result of balancing between the dielectrophoretic force and the gravity/buoyancy, which allows to analyze the cell activity.

Relating to the analysis of the cell activity, Japanese patent publication 2003-224 discloses an apparatus for concentrating living bacteria. The apparatus comprises a memory unit which stores a table for measuring the activation level. In accordance with an input data of a microorganism type and an electrical conductivity of a suspension, a processing control unit of the apparatus reads out an optimal frequency for measuring the activity. By applying an AC voltage with the above-frequency, the living bacteria may be concentrated.

SUMMARY OF INVENTION

At first, the analyzing system for the dielectrophoretic behavior disclosed in Japanese patent publication 2001-500252 serves to figure out the frequency of AC voltage suitable just for attracting the cell towards the electrode. Therefore, it is not possible to analyze a characteristics-frequency directly relating to a relaxation frequency of a frequency spectrum of a complex permittivity/complex electric conductivity of the cell. Here, the characteristics-frequency is a boundary frequency at which a dielectrophoretic force is switched from a repulsive force to an attractive force.

Therefore, for example, it is difficult to accurately identify the dielectric characteristics sensitive to the cell activity. Also, such an analysis system is not useful for any manipulation with the repulsive dielectrophoretic force to move the cells.

Secondly, the above manipulation system requires very troublesome procedures.

According to the above method, at first, a researcher has to prepare the apparatus disclosed in Japanese patent publication 2001-500252 and then using the apparatus he has to identify the specific conductor gathering the cells contained in the chamber, and determine the type of the cells, and finally figure out a suitable AC frequency for the manipulation. Then, the apparatuses disclosed in =Japanese patent publication 5-137576, Japanese patent publication 2004-522452, Japanese patent publication 2003-66004, Japanese patent publication 2005-224171, and Japanese patent publication 2003-224 should be prepared to carry out the cell fusion, the fractionation of the microparticles, the analysis of the cell activity and the cell concentration.

As stated above, several kinds of apparatuses should be prepared, and several procedures should be performed, thus the system is troublesome.

Thirdly, the above manipulating system results in poor optimization of the frequency suitable to attract a particulate.

Some cell manipulations may require to select a single cell to be manipulated. However, the AC frequency determined by the apparatus disclosed in Japanese patent_publication 2001-500252 is for attracting a specific type of cells (cell group), and not for an individual cell. Therefore, according to the prior arts, it is not possible to manipulate the selected single with the optimized AC frequency.

Considering the above first to third drawbacks, they clearly show the difficulty in selecting a single cell and determining an optimal AC frequency for providing the desired motions to the selected cell in order to manipulate it.

Next, the problems relating to the manipulation of the cell fractionation will be explained.

As stated above, the apparatus disclosed in Japanese patent publication 2001-500252 fractionates the cell types with the specific characteristics of each cell type. This method will not allow to select a single cell to be fractionated from a certain cell group, although it will be capable of gathering the cell group itself. In addition, the method disclosed in Japanese patent publication 2004-522452 will also face the same problem.

The objective of the present invention is to solve the above problems. The present invention further provides a method for analyzing characteristics of a particulate and an apparatus for the same, which allows to select a single cell, determine an optimal AC frequency for providing desired motions to the selected cell and easily manipulate it.

The present invention is not limited to the cell manipulation, and it may be used for other microparticles such as a polymer microparticle and a liposome. Further, a method for analyzing characteristics of a microparticle and an apparatus for the same according to the present invention are capable of manipulating not only the solid microparticle, but also the micro region comprising one type of liquid formed in other type of liquid.

In addition, the present invention provides a method for analyzing characteristics of a particulate and an apparatus for the same, which allows to select a cell and fractionate only the selected cell.

Further, the present invention provides a method for analyzing characteristics of a particulate and an apparatus for the same, which allows to select a cell and easily analyze an activation level of the selected cell. This results in easily constructing a data inside the table for measuring the activation level, which is used in the apparatus disclosed in Japanese patent publication 2003-224.

The present invention provides a method for analyzing characteristics of a particulate, comprising: selecting at least one particulate in a fluid; positioning said selected particulate in the vicinity of a pair of electrodes; applying a programmed voltage signal for generating a spatially inhomogeneous electric field between said pair of electrodes; detecting the movement of the particulate while applying said programmed voltage signal to create a time-series data corresponding to said movement of the particulate; and analyzing the characteristics of said particulate based on said time-series data.

According to one embodiment of the analysis method for the particulate characteristics of the present invention, said time-series data is a video data by capturing said movement of the particulate.

According to another embodiment of the analysis method for the particulate characteristics of the present invention, said time-series data is a time variation of impedance between said electrodes.

According to another embodiment of the analysis method for the particulate characteristics of the present invention, said video data further comprises a recording time data indicating capturing period.

According to another embodiment of the analysis method for the particulate characteristics of the present invention, said step of detecting the movement of the particulate includes storing said video data with said recording time data in a memory device.

According to another embodiment of the analysis method for the particulate characteristics of the present invention, said step of analyzing the characteristics of the particulate includes displaying said video data with said recording time data in a monitor.

According to another embodiment of the analysis method for the particulate characteristics of the present invention, said step of detecting the movement of the particulate includes storing the time variation data of impedance between said electrodes in a memory device.

According to another embodiment of the analysis method for the particulate characteristics of the present invention, said step of analyzing the characteristics of the particulate includes displaying the time variation data of impedance between said electrodes in a monitor.

According to another embodiment of the analysis method for the particulate characteristics of the present invention, said step of analyzing the characteristics of the particulate includes determining a stagnant time during which the selected particulate stays in the vicinity of one of said electrodes on the basis of said video data displayed in said monitor.

According to another embodiment of the analysis method for the particulate characteristics of the present invention, said step of analyzing the characteristics of the particulate includes: setting an upper threshold and a lower threshold corresponding to a change rate of said detected impedance; and determining the time from when said change rate exceeds the one of thresholds to when it exceeds the other.

According to another embodiment of the analysis method for the particulate characteristics of the present invention, step of analyzing the characteristics of the particulate includes calculating on the basis of the determined time a boundary frequency at which a dielectrophoretic force to said selected particulate is switched from an attractive force to a repulsive force.

According to another embodiment of the analysis method for the particulate characteristics of the present invention, said step of analyzing the characteristics of the particulate includes calculating on the basis of the determined time a boundary frequency at which a dielectrophoretic force to said selected particulate is switched from an attractive force to a repulsive force.

According to another embodiment of the analysis method for the particulate characteristics of the present invention, said particulate is an oval sphere.

According to another embodiment of the analysis method for the particulate characteristics of the present invention, said particulate is hollow.

According to another embodiment of the analysis method for the particulate characteristics of the present invention, said particulate has a complex permittivity different from the fluid surrounding said particulate.

According to another embodiment of the analysis method for the particulate characteristics of the present invention, said particulate has a different frequency spectrum of complex permittivity from the fluid surrounding said particulate.

According to another embodiment of the analysis method for the particulate characteristics of the present invention, said programmed voltage signal comprises an angle-modulated waveform.

According to another embodiment of the analysis method for the particulate characteristics of the present invention, said angle-modulated waveform is a frequency-modulated waveform.

According to another embodiment of the analysis method for the particulate characteristics of the present invention, said angle-modulated waveform is a phase modulated waveform.

According to another embodiment of the analysis method for the particulate characteristics of the present invention, said programmed voltage signal has an instantaneous frequency of 1 Hz to 10 GHz.

According to another embodiment of the analysis method for the particulate characteristics of the present invention, said programmed voltage signal has a modulating frequency of 100 kHz or less.

According to another embodiment of the analysis method for the particulate characteristics of the present invention, said pair of electrodes comprises a protrusion.

According to another embodiment of the analysis method for the particulate characteristics of the present invention, said pair of electrodes is in almost V-shaped arrangement.

According to another embodiment of the analysis method for the particulate characteristics of the present invention, said pair of electrodes independently moves each other or moves together in the fluid.

According to another embodiment of the analysis method for the particulate characteristics of the present invention, at least one of said electrodes moves independently from a container receiving the fluid surrounding said particulate or moves together with said container.

According to another embodiment of the analysis method for the particulate characteristics of the present invention, at least one of said electrodes moves in the same direction as the movement of the container receiving the fluid surrounding said particulate.

According to another embodiment of the analysis method for the particulate characteristics of the present invention, at least one of said electrodes moves in the different direction from the movement of the container receiving the fluid surrounding said particulate.

According to another embodiment of the analysis method for the particulate characteristics of the present invention, at least one of said electrodes moves together with the container receiving the fluid surrounding said particulate.

Yet another embodiment of the analysis method for the particulate characteristics of the present invention includes: moving said pair of electrodes after analyzing the characteristics of the particulate.

Yet another embodiment of the analysis method for the particulate characteristics of the present invention includes: providing a voltage between said electrodes after analyzing the characteristics of the particulate.

Yet another embodiment of the analysis method for the particulate characteristics of the present invention includes: gathering said selected particulate after analyzing the characteristics of the particulate.

The present invention provides an apparatus for analyzing characteristics of a particulate comprising: a chamber for receiving a suspension containing a particulate; a pair of electrodes positioned in said suspension; a voltage device for applying a programmed voltage signal between the electrodes; a capturing device for capturing the area containing at least the tip of the electrode; and a monitor for displaying an video data with said capturing device.

The present invention provides an apparatus for analyzing characteristics of a particulate comprising: a chamber for receiving a suspension containing a particulate; a pair of electrodes positioned in said suspension; a device for applying a programmed voltage signal between the electrodes; and an impedance detector for detecting an impedance between said electrodes to create a time variation data of said impedance.

One embodiment of the analysis apparatus for the particulate characteristics of the present invention further comprises a memory device for storing said video data.

Another embodiment of the analysis apparatus for the particulate characteristics of the present invention further comprises a memory device for storing a time-series data of said detected impedance.

Yet another embodiment of the analysis apparatus for the particulate characteristics of the present invention further comprises an input device for inputting an upper threshold and a lower threshold corresponding to the impedance amplitude between the electrodes into said memory device.

Yet another embodiment of the analysis apparatus for the particulate characteristics of the present invention further comprises a processing unit for calculating an interval time between when the detected impedance exceeds the upper threshold and when it exceeds the lower threshold.

According to another embodiment of the analysis apparatus for the particulate characteristics of the present invention, said processing unit calculates on the basis of the calculated time a boundary frequency at which a dielectrophoretic force to said selected particulate is switched from an attractive force to a repulsive force.

According to another embodiment of the analysis apparatus for the particulate characteristics of the present invention, said monitor displays said video data with an recording time of said capturing device. Yet another embodiment of the analysis apparatus for the particulate characteristics of the present invention further comprises a processing unit and an input device for inputting an input data into said processing unit, wherein said processing unit calculates a boundary frequency at which a dielectrophoretic force to a particulate is switched from an attractive force to a repulsive force on the basis of the input data through said input device, wherein said input data is a stagnant time during which the particulate stays in the vicinity of one of said electrodes on the basis of the video data of said monitor and the recording time data of the capturing device.

According to another embodiment of the analysis apparatus for the particulate characteristics of the present invention, said particulate is an oval sphere.

According to another embodiment of the analysis apparatus for the particulate characteristics of the present invention, said particulate is hollow.

According to another embodiment of the analysis apparatus for the particulate characteristics of the present invention, said particulate has a complex permittivity different from the fluid surrounding said particulate.

According to another embodiment of the analysis apparatus for the particulate characteristics of the present invention, said particulate has a different frequency spectrum of complex permittivity from the fluid surrounding said particulate.

According to another embodiment of the analysis apparatus for the particulate characteristics of the present invention, said programmed voltage signal comprises an angle-modulated waveform.

According to another embodiment of the analysis apparatus for the particulate characteristics of the present invention, said angle-modulated waveform is a frequency-modulated waveform.

According to another embodiment of the analysis apparatus for the particulate characteristics of the present invention, said angle-modulated waveform is a phase modulated waveform.

According to another embodiment of the analysis apparatus for the particulate characteristics of the present invention, said programmed voltage signal has an instantaneous frequency of 1 Hz to 10 GHz.

According to another embodiment of the analysis apparatus for the particulate characteristics of the present invention, said programmed voltage signal has a modulating frequency of 100 kHz or less.

According to another embodiment of the analysis apparatus for the particulate characteristics of the present invention, said pair of electrodes comprises a protrusion.

According to another embodiment of the analysis apparatus for the particulate characteristics of the present invention, said pair of electrodes is in almost V-shaped arrangement.

According to another embodiment of the analysis apparatus for the particulate characteristics of the present invention, said pair of electrodes independently moves each other or moves together in the fluid.

According to another embodiment of the analysis apparatus for the particulate characteristics of the present invention, at least one of said electrodes moves independently from a container receiving the fluid surrounding said particulate or moves together with said container.

According to another embodiment of the analysis apparatus for the particulate characteristics of the present invention, at least one of said electrodes moves in the same direction as the movement of the container receiving the fluid surrounding said particulate.

According to another embodiment of the analysis apparatus for the particulate characteristics of the present invention, at least one of said electrodes moves in the different direction from the movement of the container receiving the fluid surrounding said particulate.

According to another embodiment of the analysis apparatus for the particulate characteristics of the present invention, at least one of said electrodes moves together with the container receiving the fluid surrounding said particulate.

According to another embodiment of the analysis apparatus for the particulate characteristics of the present invention, said device for applying a programmed voltage signal between the electrodes comprises a waveform generator.

According to another embodiment of the analysis apparatus for the particulate characteristics of the present invention, said device for applying a programmed voltage signal between the electrodes comprises a frequency modulator.

According to another embodiment of the analysis apparatus for the particulate characteristics of the present invention, said device for applying a programmed voltage signal between the electrodes comprises a voltage amplifier.

According to another embodiment of the analysis apparatus for the particulate characteristics of the present invention, said device for applying a programmed voltage signal between the electrodes is capable of applying a DC voltage therebetween.

DETAILED DESCRIPTION OF THE INVENTION

Figure 1:
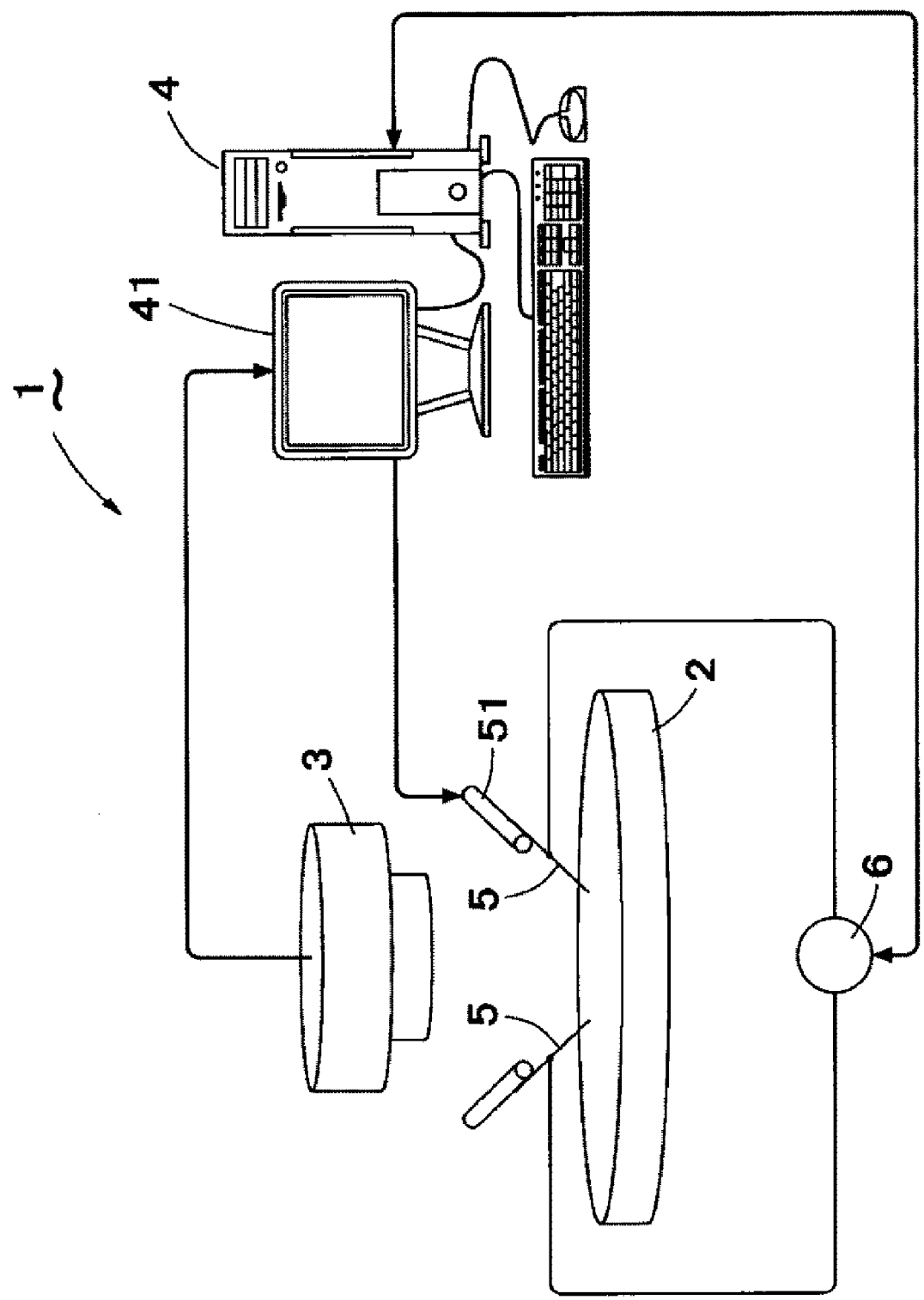
FIG. 1 is a diagram of an analysis apparatus for the particulate characteristics according to the present invention.

A method for analyzing characteristics of a particulate according to the present invention allows to efficiently analyze the characteristics of a desired particulate.

According to one embodiment of the present invention, a time-series data corresponding to the movement of a particulate is created as a video data by using a capturing device in order to analyze the characteristics of the particulate. The video data may include a recording time data indicating capturing period. The video data is displayed in the monitor. The recording time data may be also displayed together with the video data in the monitor. This results in easily determining a time during which the monitor displays a certain movement of the particulate. For example, a time during which the particulate is almost stationary in the tip of one of electrodes used for applying a programmed voltage signal can be identified by watching the monitor.

According to another embodiment of the present invention, the time-series data of the particulate movement is a time variation of the impedance between the electrodes used for applying the programmed voltage signal to the particulate. The impedance differs between when the particulate stays in the vicinity of the electrode tip and when it is away from the electrode tip. As a result, the particulate movement indicating whether the particulate positions in the vicinity of the electrode tip or not is easily and accurately determined.

In order to detect the impedance-change, a threshold may be used. For example, an upper threshold and a lower threshold corresponding to the impedance-change may be set. Then, an interval time between when the impedance-change exceeds the upper threshold and when it exceeds the lower threshold is designated as a time during which the particulate stays in the electrode tip.

Applying a programmed voltage signal induces dielectrophoretic force to the particulate. The dielectrophoretic force works as an attractive force or a repulsive force to the particulate. When the dielectrophoretic force works as the attractive force to the particulate, the particulate approaches one of the electrodes used for applying the programmed voltage signal. In contrast, when the dielectrophoretic force works as the repulsive force to the particulate, the particulate moves away from one of the electrodes used for applying the programmed voltage signal.

When the programmed voltage signal is an angle-modulated waveform, the dielectrophoretic force to the particulate alternately works as the attractive force and the repulsive force to the particulate. As a result, the particulate repeatedly and cyclically approaches and moves away from one of electrodes used for applying the programmed voltage signal.

While switching the particulate movement from approach to one of the electrodes used for applying the programmed voltage signal to departure from it, the particulate is almost stationary in the vicinity of the tip of either electrode. The time period during which the particulate is stationary can be easily determined by the video data displayed in the monitor and the time variation of the impedance between electrodes as described above.

A boundary frequency at which the dielectrophoretic force is switched from the attractive force to the repulsive force can be calculated based on the stagnant time of the particulate around the tip of the electrode, which is determined by the video data displayed in the monitor and the time variation of the impedance between electrodes.

Use of a frequency-modulated waveform or phase modulated waveform as an angle-modulated waveform in the programmed voltage signal application will cause the periodical movement described above of the particulate.

In specific embodiment of the analysis method for the particulate characteristics according to the present invention, the programmed voltage signal is from 1 Hz to 10 GHz. According to another embodiment thereof, the programmed voltage signal is 100 kHz or less.

The method of the present invention is capable of analyzing characteristics of the particulate in any shape, such as an oval sphere or hollow. A complex permittivity of the particulate different from a surrounding fluid allows to preferably execute the analysis method of the present invention. Alternatively, the particulate may have a different frequency spectrum of complex permittivity from a surrounding fluid. In this case the analysis method of the present invention will also work well.

The pair of electrodes used for applying the programmed voltage signal may be in a needle shape. Alternatively, the electrodes may be provided by printed electrodes in the bottom of the chamber (the bottom of the container) receiving the particulate.

In some embodiments of the analysis method for the particulate characteristics of the present invention, the pair of the needle electrodes is almost symmetrically-positioned by forming nonparallel lines (i.e., almost "V" shape) in the chamber. According to another embodiment, the printed or on-chip electrodes with protrusions may be used.

In the analysis method for the particulate characteristics according to the present invention, the pair of electrodes may be moved in various manners.

In some embodiments of the analysis method for the particulate characteristics of the present invention, each electrode independently moves each other. According to another embodiment, the electrodes move together.

In another embodiment, at least one of the electrodes moves in the same direction as the movement of the chamber receiving the particulate. In another embodiment, at least one of the electrodes moves in the different direction from the movement of the chamber receiving the particulate.

These moving modes are appropriately combined or selected on demand from users using the present invention.

The moving operation described above of the electrodes and container is carried out for the purpose of not only selecting the targeted particulate but also manipulating the particulate after the calculation for the boundary frequency. Through the above movement of the electrodes and the container, the particulate may be moved to any desired position. In another embodiment, a DC voltage may be further applied to the particulate. In addition, the particulate may be collected to a certain area.

The present invention provides a preferable apparatus for analyzing characteristics of the particulate in order to carry out the above-mentioned method. According to the apparatus of the present invention, the characteristics of the particulate can be easily and quickly measured and analyzed.

Hereinafter, a method for analyzing characteristics of the particulate and an apparatus for the same according to the present invention will be explained with reference to the drawings. In addition, in the explanation below, the object for analyzing the characteristics will be a cell. However, the present invention is not limited thereto, and it can be applied to analyze the characteristics of other objects other than the cell.

FIG. 1 is a diagram showing one embodiment of an apparatus for analyzing characteristics of the particulate according to the present invention.

The apparatus for analyzing characteristics of the particulate (Hereinafter, it refers to as "analyzing apparatus") (1) comprises a chamber (2) for receiving a suspension containing a particulate, a detector (CCD camera-equipped microscope) (3) placed above the chamber (2) as well as capable of obtaining a time-series data of an observation image inside the chamber (2), an analyzer (computer) (4) for recording and processing the data obtained by the detector (3), a pair of needle electrodes (5) to be inserted in the suspension layer inside the chamber (2) and a programmed voltage signal source (6) electrically connected to the needle electrode (5).

The analyzer (4) incorporates a memory (memory device) which is the same as what any personal computer commercially available has.

The needle electrodes (5) are connected to arms respectively (51) used for moving or rotating the needle electrodes (5). An electric motor moves the arms (51). It is preferable to input a rotational angle and a rotational direction of the electric motor with input means (ex. keyboard) of the analyzer (4) in order to decide a moving distance and a moving direction of the arms (51).

In the embodiment shown in FIG. 1, each needle electrode (5) is independently controlled. Thus, only one of the needle electrodes may be moved. In addition, the pair of the needle electrodes (5) may be moved together.

The programmed voltage signal source (6) is capable of outputting an angle-modulated waveform such as a frequency-modulated waveform and a phase modulated waveform. In the embodiment, a device to generate an arbitrary waveform is used as the programmed voltage signal source (6). The waveform generator integrally comprises an AC power source and a modulator for modulating the frequency of AC voltage from the AC power source. However, the AC power source and the modulator may be prepared separately. The waveform generator may further comprise a voltage amplifier, in addition to the programmed voltage signal source (6). Here, the term "programmed" means that various waveforms can be desirably generated by substituting values into parameters of waveform equations.

In addition, the analyzer (4) may be connected to an output port of the programmed voltage signal source (6) to use it as an oscilloscope and to synchronize the timing of voltage input and data acquisition.

An image data (video data) from the detector (3) is sequentially sent to the analyzer (4) and stored in a memory device incorporated in the analyzer (4). As a result, the image data from the detector (3) in time-series manner is stored (4) in the analyzer (4). A monitor (41) of the analyzer (4) displays the image data sent from the detector (3). In the monitor (41), a time data corresponding to the image data displayed in the monitor (41) (the number of images of the image data, a capturing period of the detector (3) and so on) is further displayed.

Figure 2:
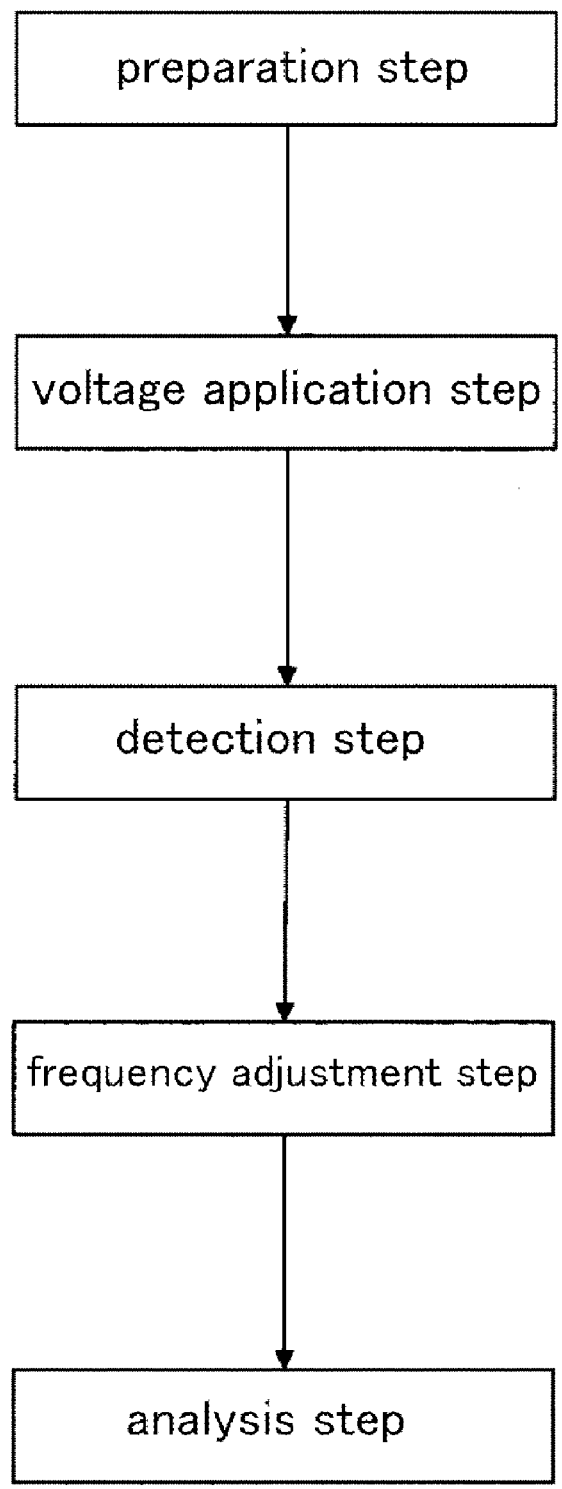
FIG. 2 is an overview flowchart showing an analysis method for the particulate characteristics according to the present invention.

FIG. 2 is an overview flowchart showing a method for analyzing characteristics of the particulate according to the present invention. In the explanation below, the embodiment using the analyzing apparatus (1) shown in FIG. 1 is explained. However, the method for analyzing the characteristics of the particulate of the present invention is not limited thereto, and it can be applied to the apparatuses having other structures.

The method for analyzing the characteristics of the particulate (Hereinafter, it refers to as "analyzing method") comprises a preparation step, a voltage application step, a detection step, a frequency adjustment step and an analysis step. The operation from the preparation step to the adjustment step may be repeated until determining appropriate ranges of an instantaneous frequency and a modulating frequency for the analysis step. Although the example shown in FIG. 2 carries out the detection step after the voltage application step, these two steps may be interchanged.

Figure 3:
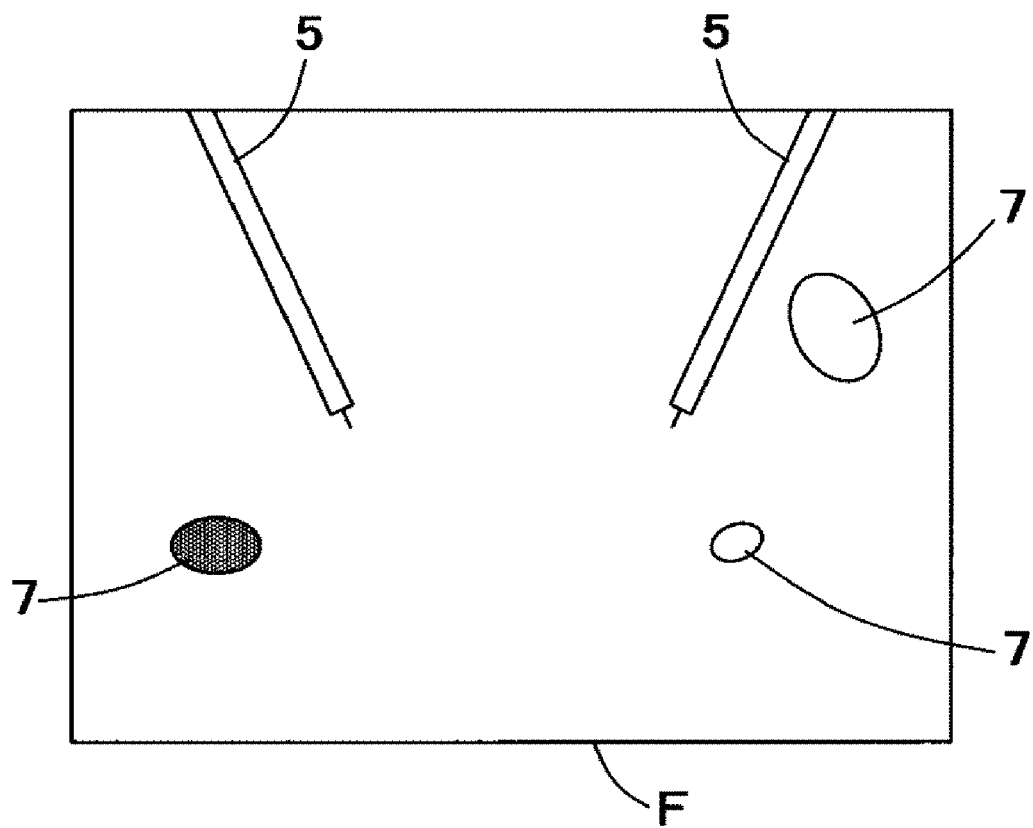
FIG. 3 shows a microparticle selection step of an analysis method for the particulate characteristics according to the present invention.

FIG. 3 shows the field of the image (i.e. view field) obtained from the observation device (3). In FIG. 3, the field inside a rectangular frame is a view field (F). The view field is shown in the monitor (41).

In the view field (F), the pair of needle electrodes (5) is displayed. The needle electrodes (5) are coated with a dielectric material except the tips thereof to generate an electric field between the tips. In addition, the pair of needle electrodes (5) is positioned in the suspension layer with V-shaped arrangement. The tip to tip distance of the needle electrodes (5) is the shortest.

In the example shown in FIG. 3, three cells (7) are displayed in the view field (F). The cells (7) are surrounded by the suspension. The suspension has a complex permittivity different from the cell. Alternatively, the suspension may have a different frequency spectrum of complex permittivity from the cell (7).

In the preparation step, one of the cells (7) displayed in the view field (F) is selected. Here, the hatched cell (7) is selected. If there is no desired cell (7) in the view field (F), the observation field may be changed to observe other view field (F).

Figure 4:
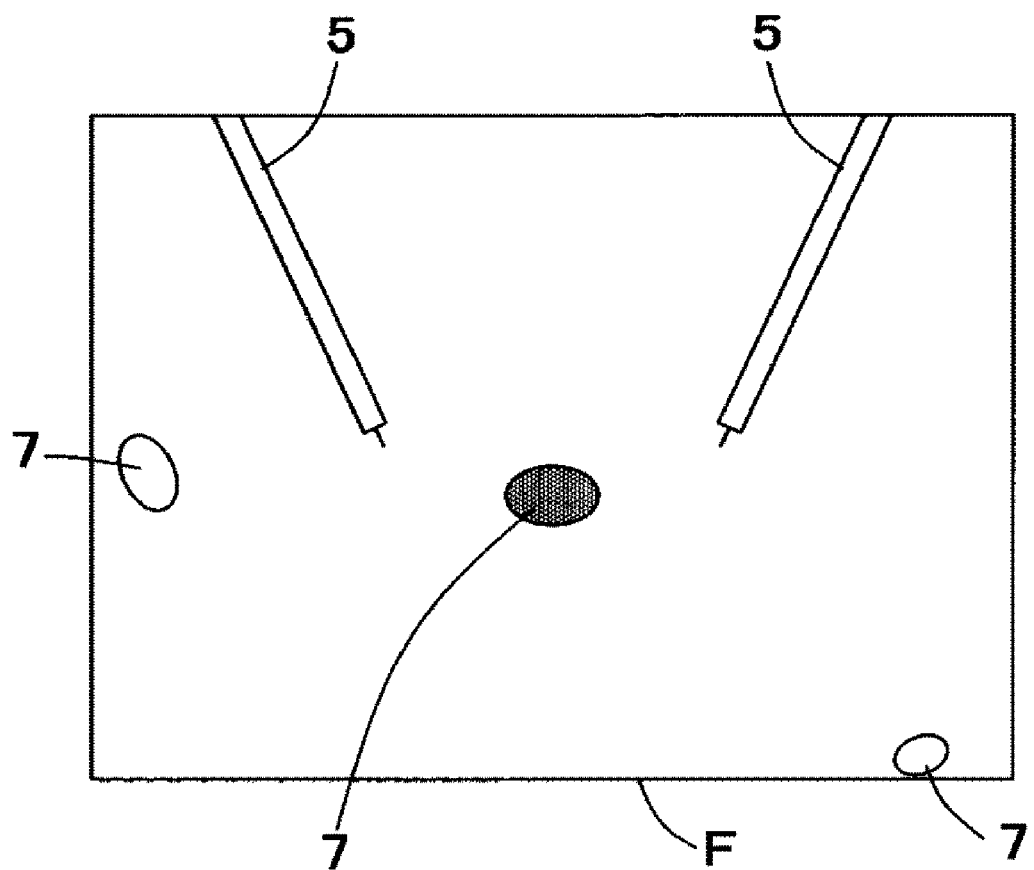
FIG. 4 shows a microparticle positioning step of an analysis method for the particulate characteristics according to the present invention.

FIG. 4 shows the image displayed in the view field (F) after selecting the cell (7).

After a single cell (7) is selected, the needle electrodes (5) are moved to place the selected cell (7) in the vicinity of the tips of the needle electrodes (5) and align between the tips as long as the electric field between the needle electrodes (5) is effective. At this time, in accordance with the movement of the needle electrodes (5), the observation device (3) is controlled to move the view field (F).

Figure 5:
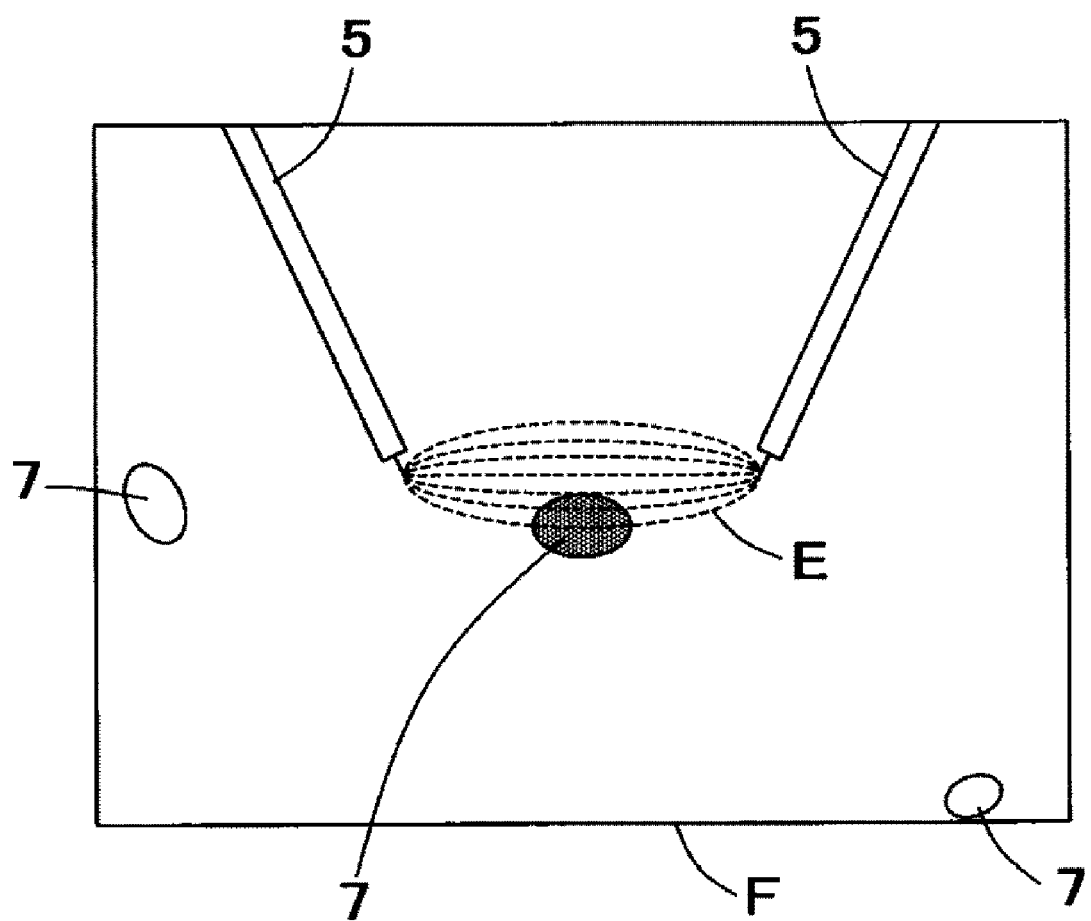
FIG. 5 shows the application of the programmed voltage signal from the source to the pair of electrodes.

FIG. 5 shows the application of the programmed voltage signal from the source (6) to the pair of electrodes (5). In this stage, the electric field strength is stronger in the vicinity of the tips of needle electrodes (5), while it becomes weaker with distance from the tips of the needle electrodes (5), which results in a spatially inhomogeneous electric field.

In the present embodiment, as the signal waveform (angle-modulated waveform), the frequency-modulated waveform shown in the following equation is used.

$$E = E_0 \sin\left(2\pi f_c t + \frac{\Delta f}{f_m} \sin(2\pi f_m t)\right) \quad \text{[equation 1]}$$

Here, $E_0$ is an amplitude of the applied electric field. The instantaneous frequency $f(t)$, which is calculated by temporally differentiating the argument of the sine function of the above equation, is shown as the following equation.

$$f(t) = f_c + \Delta f \cos(2\pi f_m t) \quad \text{[equation 2]}$$

According to the above equation 2, it is shown that the instantaneous frequency is ranged from $f_c - \Delta f$ to $f_c + \Delta f$ and the modulating frequency is $f_m$ when the frequency-modulated waveform shown in the equation 1 is applied.

While the frequency-modulated waveform shown in the equation 1 is applied, the dielectrophoretic force works to the cell (7) shown in FIG. 5, and the dielectrophoretic force is shown as the following equation.

$$F_d = 2\pi a^3 Re(\in_s) Re[K(f(t))] grad(0.5 E_0^2) \quad \text{[equation 3]}$$

$$K(f(t)) = (\in_p - \in_s)/(\in_p + 2\in_s) \quad \text{[equation 4]}$$

Here, Fd is the dielectrophoretic force for moving the cell (7). "a" represents the radius of the cell (7) when the cell (7) is sphere. Re(x) represents a real part of a complex number x. In addition, K is called "Clausiuis-Mossotti function" which is a function of the instantaneous frequency f(t). $\in_p$ is the complex permittivity of the cell (7), and $\in_s$ is the complex permittivity of the solvent. Here, the real part of the complex permittivity of a water solvent is generally regarded as a constant number when the instantaneous frequency is ranged from 1 Hz to 10 GHz.

In addition, instead of the frequency-modulated waveform, a phase modulated waveform shown as the following equation may be used.

$$E = E_0 \sin(2\pi f_c t + 2\pi s(t)) \quad \text{[equation 5]}$$

At this time, the instantaneous frequency f(t) is shown as the following equation.

$$f(t) = f_c + \frac{ds(t)}{dt} \quad \text{[equation 6]}$$

The magnitude and direction of the above force Fd depends on the instantaneous frequency f(t) through Clausiuis-Mossotti function K. For the detail, a boundary frequency $f_0$ at which the dielectrophoretic force is switched from the repulsive force to the attractive force is determined by a dielectric relaxation frequency which is a peak frequency in the frequency spectrum of the imaginary part of the complex permittivity of the cell (7).

Figure 6:
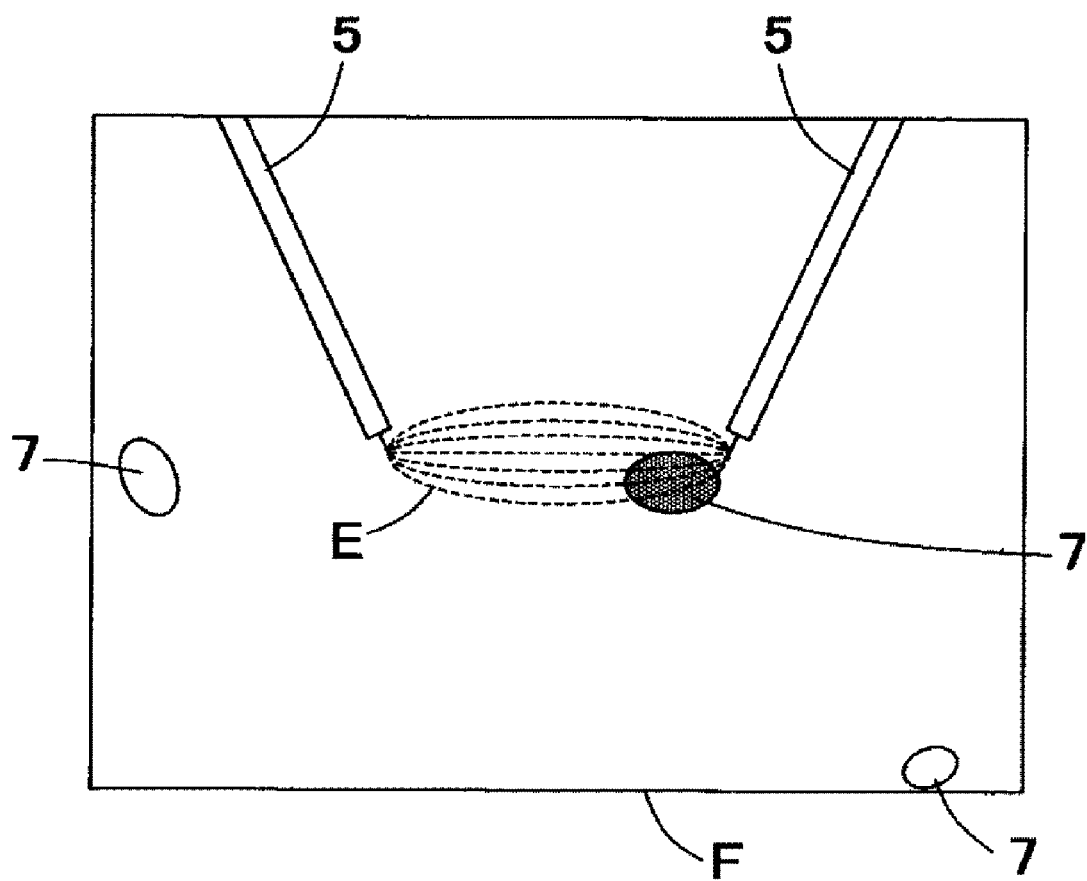
FIG. 6 shows the view field (F) when the instantaneous frequency is in higher frequency range (the value of Clausiuis-Mossotti function is negative).

FIG. 6 shows the view field (F) when the dielectrophoretic force works as the attractive force to the cell (7). Therefore, the cell (7) is held in the area between the tips of the needle electrodes (5) or close to one of the needle electrodes (5), where stronger electric field exists.

Figure 7:
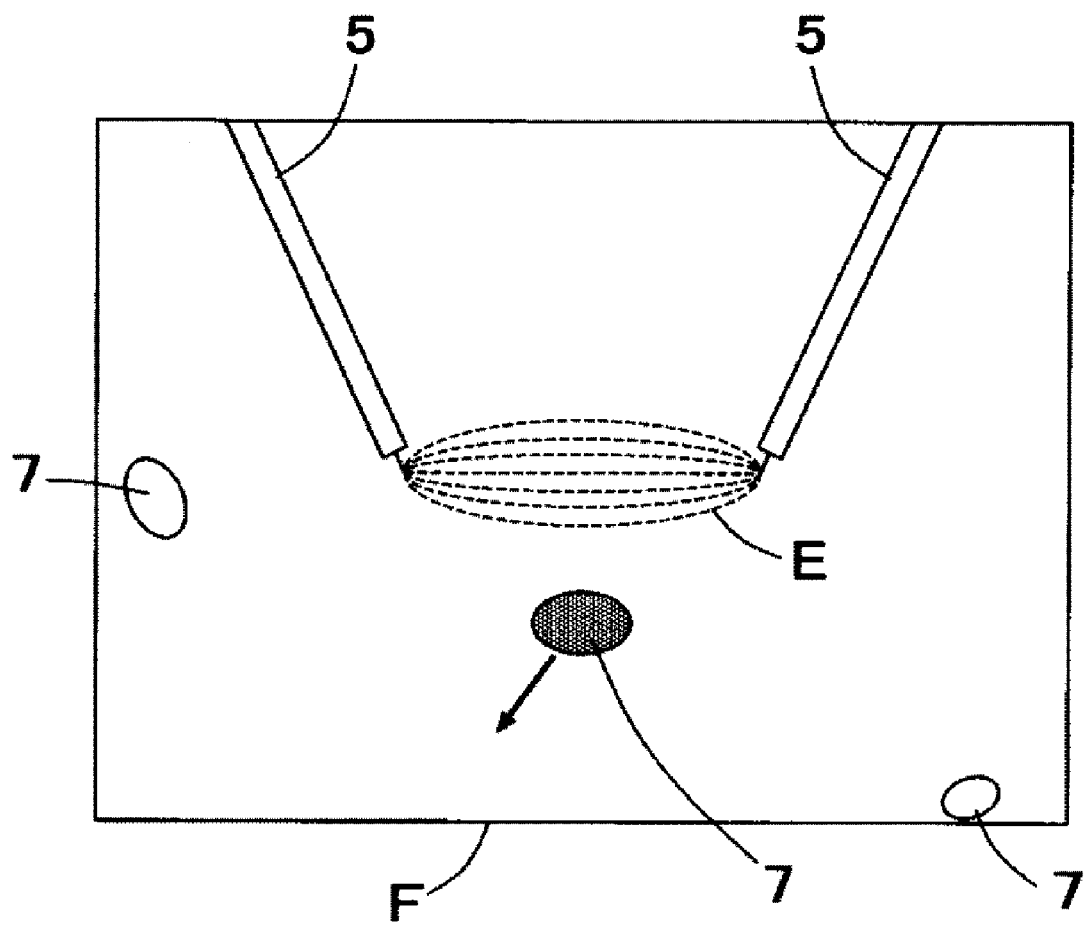
FIG. 7 shows the view field (F) when the instantaneous frequency is in lower frequency range (the value of Clausiuis-Mossotti function is positive).

FIG. 7 shows the view field (F) when the dielectrophoretic force works as the repulsive force to the cell (7). Therefore, the cell (7) is pushed and moved outside the electric field (E).

Figure 8:
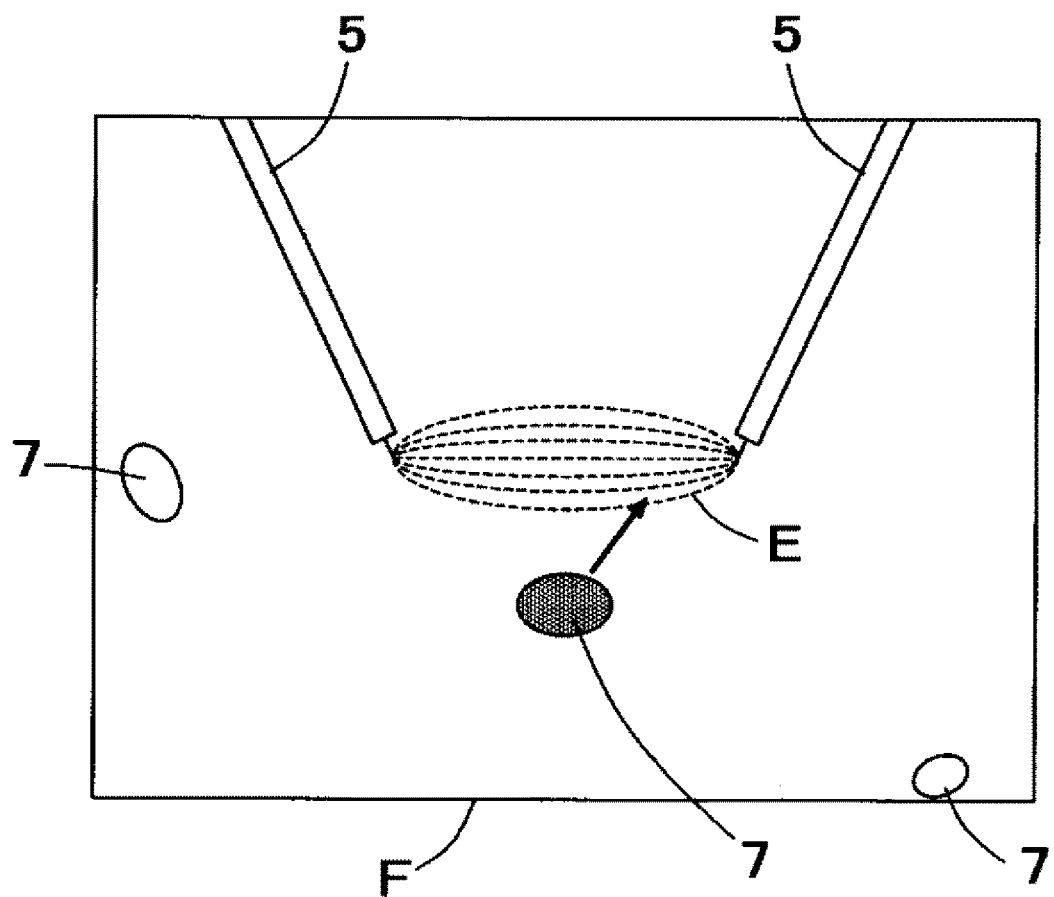
FIG. 8 shows the view field (F) when the value of Clausiuis-Mossotti function is changed from positive to negative.

FIG. 8 shows the view field (F) when the instantaneous frequency is in a transient range where the value of Clausiuis-Mossotti function is changed from positive to negative. At this time, the dielectrophoretic force to the cell (7) is switched to the attractive force. Therefore, the cell (7) is moved again to be attracted between the tips of the needle electrodes (5).

As shown in the equation 2, the instantaneous frequency in the frequency-modulated wave cyclically goes up and down with a period $1/f_m$, depending on the modulating frequency $f_m$. Thus, when the modulating frequency is 0.1 Hz, the movement of the cell (7) interchanges in 10 seconds intervals so that the cell (7) repeatedly approach and move away from the tips of needle electrodes (see FIGS. 6 and 7), because of cyclic change in the instantaneous frequency. In addition, the modulating frequency is preferably set to 100 kHz or less in order to observe the movement of the cell (7).

In the analysis step with applying the frequency-modulated wave, the stagnant time during which the particulate stays in the vicinity of one of the needle electrodes (5) (see FIG. 6) can be determined by the time-series data corresponding to the movement of the particulate (video data displayed in the monitor (41) of the analyzer (4)). Thus, the observer can determine the stagnant time during which the cell (7) stays in the vicinity of the tips of the needle electrodes (5) by the movement of the cell (7) and the time data displayed in the monitor (41) of the analyzer (4). Here the stagnant time is designated as "τ". In case that the time period where the instantaneous frequency changes from the maximum value $f_c + \Delta f$ to the boundary frequency $f_0$ is 0.5τ, $f_0$ may be shown as the following equation.

In addition, the boundary frequency $f_0$ may be calculated by a processing unit such as a CPU comprised in the analyzer (4) or by a hand calculation. When the processing unit in the analyzer (4) is used to calculate the boundary frequency $f_0$, for example, an input device such as a keyboard electrically connected to the analyzer (4) may be used. The stagnant time τ is inputted by the input device, and the processing unit calculates the boundary frequency $f_0$ with the following equation.

$$f_0 = f_c + \Delta f \cos(\pi f_m \tau) \quad \text{[equation 7]}$$

Significant change in the boundary frequency $f_0$ will be generally observed when an electric conductivity of the surrounded fluid is from 10 mS/m to 100 mS/m, if a cell, a liposome and a polymer microparticle is subjected to this particulate analysis. Thus, desirable range of the instantaneous frequency depends on the electric conductivity of the fluid surrounding the particulate. When the electric conductivity of the fluid is small enough comparing to the above range of the electric conductivity, $f_0$ generally exceeds 1 MHz. Thus, the minimum value of the instantaneous frequency is preferably set to more than 1 MHz. On the contrary, when the electric conductivity of the fluid is large enough comparing to the above range of the electric conductivity, $f_0$ is generally between 100 kHz to 1 MHz. Thus, the maximum value of the instantaneous frequency is preferably set to around 1 MHz.

One advantage of the present invention is that the boundary frequency can be determined in a short time. For example, when the modulating frequency of the frequency-modulated waveform is set to 0.1 Hz as mentioned above resulting in 10 seconds of cyclic period, about 3 cycles of the time-series data are enough to determine the stagnant time τ. Therefore, it will take less than 1 minute to carry the analysis. When the boundary frequency is sensitive to the electrical field application, in the case of a cell for example, shorter analysis to identify the characteristics is significantly advantageous as stated above.

Another advantage of the present invention is that the history of the change in the characteristics of the same single particulate can be tracked. For example, the instantaneous frequency is ranged from 100 kHz to 900 kHz or the modulating frequency is set to 0.1 Hz in the liposome suspension instead of the cell suspension to obtain the following result.

At first, a single liposome is targeted. The voltage signal of the modulating frequency of the above-condition is applied to the liposome by using the needle electrodes (5). As a result, the stagnant time is determined to about 5 seconds. By substituting the value to the equation 7, about 500 kHz of the boundary frequency is calculated out.

Next, an almost transparent and highly dilute stain is dropped thereto with a microinjector. As a result, water is not stained, and only the liposome wall including a hydrophobic site is selectively stained.

During the above series of operations, the electrical field is not applied, but the liposome remains identified by observation. After the stain, the same waveform voltage is applied again to measure the stagnant time. As a result of this operation, the stagnant time becomes about 3 seconds. By substituting the value to the equation 7, the boundary frequency is determined in a short time. The boundary frequency is slightly changed from the above-calculated 500 kHz to 700 kHz.

The present invention is not only applied to a semisolid microparticle such as the cell (7) or a solid microparticle, but also to a micro region comprising a liquid in order to measure the characteristics.

For example, one type of liquid (Hereinafter, referred to as "first liquid") is contained in the chamber (2) to form a solution layer. Next, the other type of liquid (Hereinafter, referred to as "second liquid") with a different electric permittivity from the first liquid is prepared. The second liquid is contained in a piston cylinder. Then, the second liquid in the piston cylinder is dropped to the chamber (2) from the above. Thus, the micro region comprising the second liquid from the piston cylinder is formed in the solution layer.

Thus, the same method of the above analysis can be used for analyzing characteristics of the micro region.

As seen above, the present invention can be applied to not only an oval sphere particle such as the cell, but also to a micro region in various shapes, such as the liquid, with different electric permittivity and/or frequency spectrum of complex permittivity from the surrounding liquid or to a hollow particle.

Next, a cell manipulation for the fractionation will be explained.

At first, the chamber (2) receiving the suspension containing one type of cell is prepared. Here, the user knows the type of the prepared cell. Then, the characteristics of the prepared cell are measured.

Next, the chamber (2) receiving the suspension containing other type of cell is prepared. Also, the user knows the type of the prepared cell. Then, the characteristics of the prepared cell are measured.

By this means, the several types of cells are measured to clearly show the differences of the stagnant time (i.e., the differences of the boundary frequency).

Figure 9:
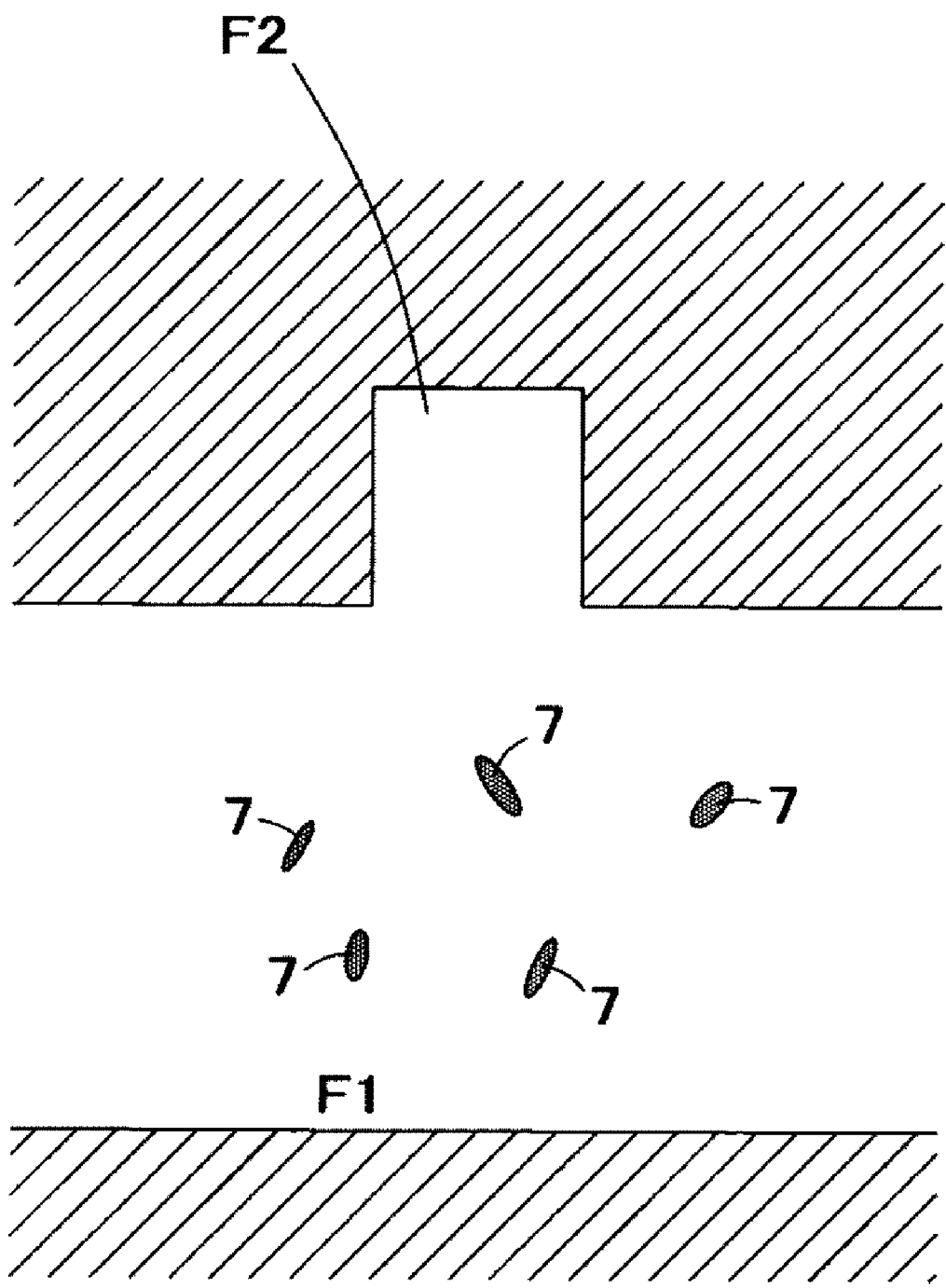
FIG. 9 shows the one example of the manipulation of cell fractionation.

FIG. 9 shows a working area where 5 types of cell are placed. In the example shown in FIG. 9, the types of cells can not be distinguished visually. Here, in FIG. 9, "cell 1" whose stagnant time is identified by using the above-procedures is selected from the 5 cells placed in the working area (F1) to move and place in a working area (F2).

Here, the frequency of the AC voltage for applying between the needle electrodes (5) is set to 500 kHz, and then the needle electrodes (5) approach each cell.

A cell is identified as "cell 1" among these cells if the cell shows the same stagnant time as the predetermined one when the pair of the needle electrodes (5) approaches to it. The cell identified as "cell 1" is moved to the working area (F2), and thus the only targeted cell can be fractionated. For delivery of the cell 1 into working area (F2), the needle electrodes (5) themselves or the microscope stage on which the chamber is placed are controlled with maintaining the repulsive force between the electrodes (5) by the frequency modulated AC voltage application. After the above manipulation of the fractionation, "cell 1" is recovered for desired analysis or cell manipulation.

The method for moving "cell 1" is not limited. For example, the needle electrodes (5) and the chamber (2) may be independently moved each other. The needle electrodes (5) and the chamber (2) may be moved in the same direction at the different speed. The needle electrodes (5) and the chamber (2) may be moved in the different direction from each other. In such a control for moving the needle electrodes (5), just either of the needle electrodes (5) may be moved.

In the above example, the cell (7) is handled in the area beyond the tips of the needle electrodes (5) with V-shaped arrangement. However, the cell (7) may be even placed inside the area from the tips of the needle electrodes (5) to their proximal ends to manipulate the cell (7) in the same manner as the above description.

Figure 10:
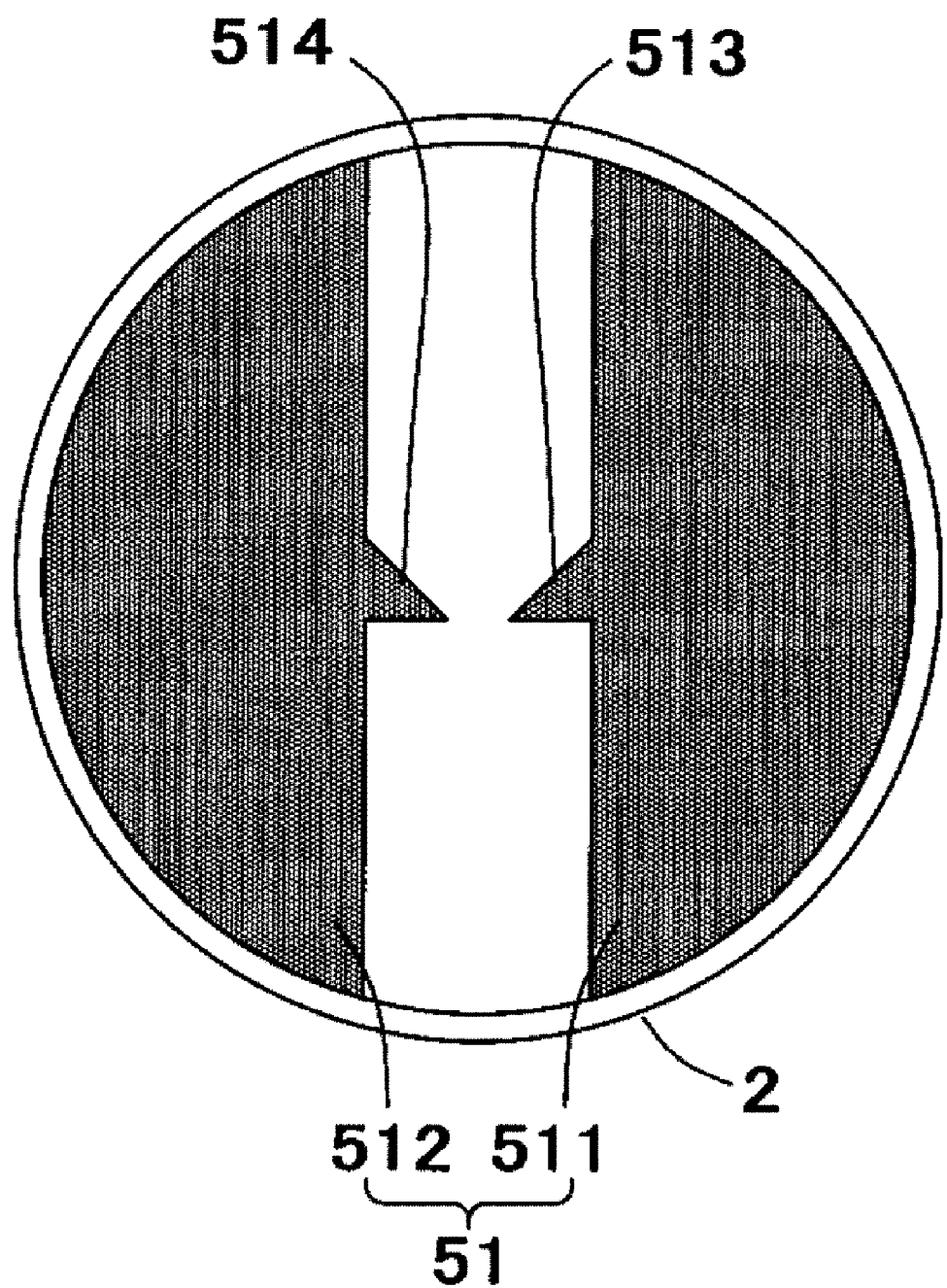
FIG. 10 shows another embodiment of the electrodes of the present invention.

FIG. 10 shows the embodiment of other electrodes.

In the above explanation, the needle electrodes (5) are used, however, the present invention is not limited thereto. As shown in FIG. 10, pattern electrodes (51) printed on the bottom surface of the chamber (2) may be used as the electrodes in the present invention.

The pattern electrodes (51) shown in FIG. 10 comprises electrode regions (511) (512) placed on the left surface and right surface of the chamber bottom at a given distance. Between the electrode regions (511) (512), triangle protrusions (513) (514) are formed. Such pattern electrodes (51) allow to generate inhomogeneous electric field between the left and right electrode regions (511) (512). This enables to carry out the same manipulations as above with moving the chamber (2) and the electrodes (51) together.

The above-mentioned method may be applied for analyzing a cell activation level.

At first, the chamber (2) receiving a suspension including cells just after being taken out of an incubator is prepared. Here, "cell 1" used in the explanation of FIG. 9 is designated as the target. After that, the relationship between the applied AC voltage frequency and the movement of "cell 1" is daily investigated.

The cell characteristics change depending on the cell activation level. Therefore, the clear relationship between the applied AC voltage frequency and the movement of "cell 1" enables to fractionate only high active cells.

In addition, the boundary frequency or the stagnant time per cell types or cell conditions is preferably stored in the recorder (4) as a database. Thus, the database for various types of cells accumulating their characteristics data results in efficient manipulation for the various types of cells (fractionation, concentration, activity level analysis and so on).

In addition, when the programmed voltage signal source (6) is capable of applying the DC voltage, the manipulation of a cell fusion may be carried out as follows. Selected cells are fractionated as mentioned above, then the fractionated cells are arranged in a line. After that, the needle electrodes (5) are controlled to approach ends of the cell line, respectively. Finally the DC voltage is applied thereto.

Figure 11:
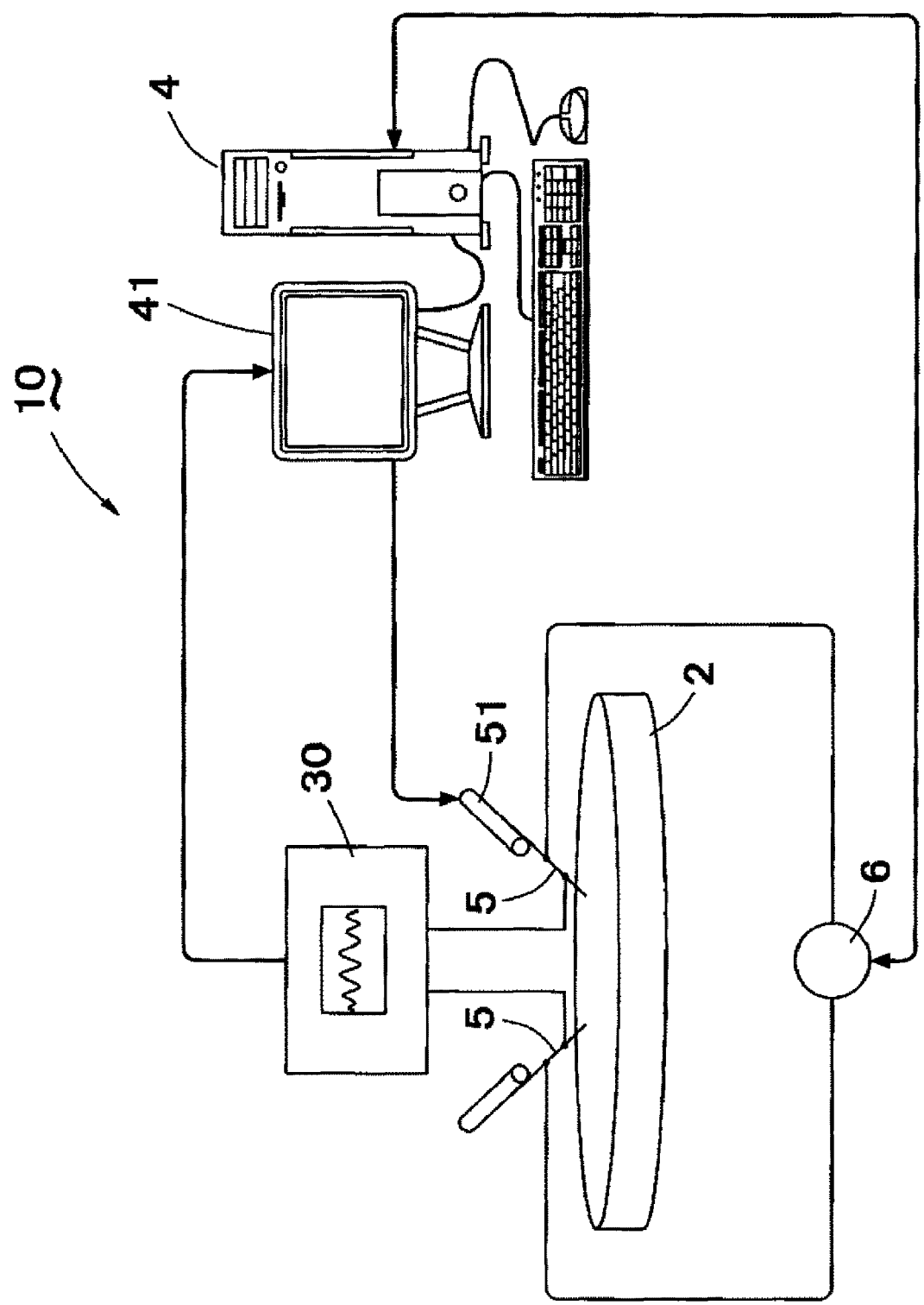
FIG. 11 shows an alternate embodiment of the analyzing apparatus shown in FIG. 1.

FIG. 11 shows an alternate embodiment of the analyzing apparatus shown in FIG. 1. The analyzing apparatus shown in FIG. 11 is also used for the same manipulation and analysis as stated above.

In the analyzing apparatus (10) shown in FIG. 11, an impedance detector (30) is used in place of the observation device (3) of the analyzing apparatus (1) shown in FIG. 1. As the impedance detector (30), for example, an impedance analyzer or a LCR meter may be used. Also, any devices capable of obtaining the time-series data of the impedance between needle electrodes (5) may be used as the impedance detector (30).

The impedance detector (30) is electrically connected to the needle electrodes (5) in order to measure the impedance between them. In the example shown in FIG. 11, the time-series data of the measured impedance is stored in the memory device incorporated in the analyzer (4) which is connected to the impedance detector (30). In addition, the monitor (41) of the analyzer (4) displays the graph of impedance amplitude as shown in FIG. 12.

Further, the impedance detector (30) itself may serve to store and/or display the time-series data of the measured impedance.

Figure 12:
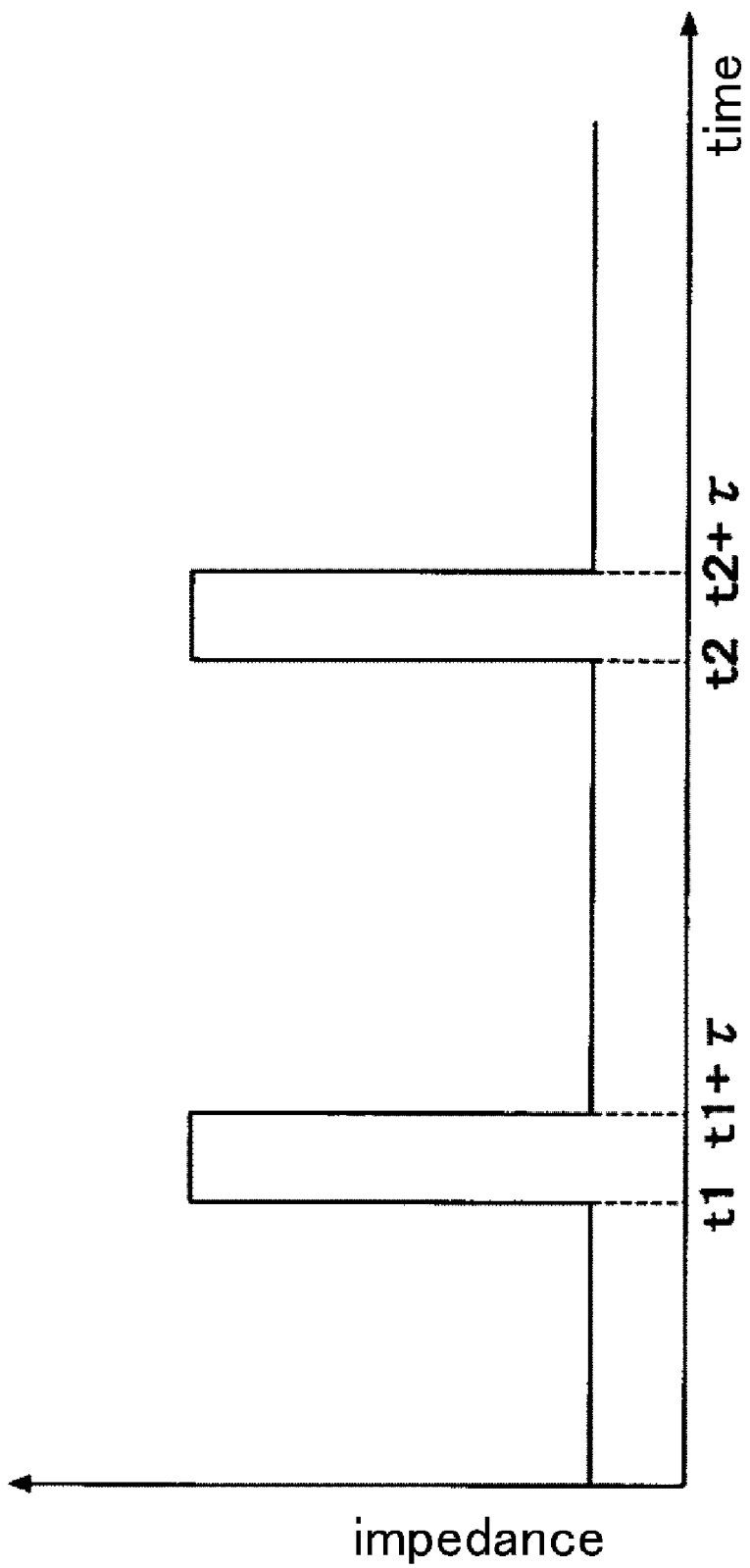
FIG. 12 shows the diagrammatic graph of the time-series data of the impedance obtained by the analyzing apparatus shown in FIG. 11.
Figure 13:
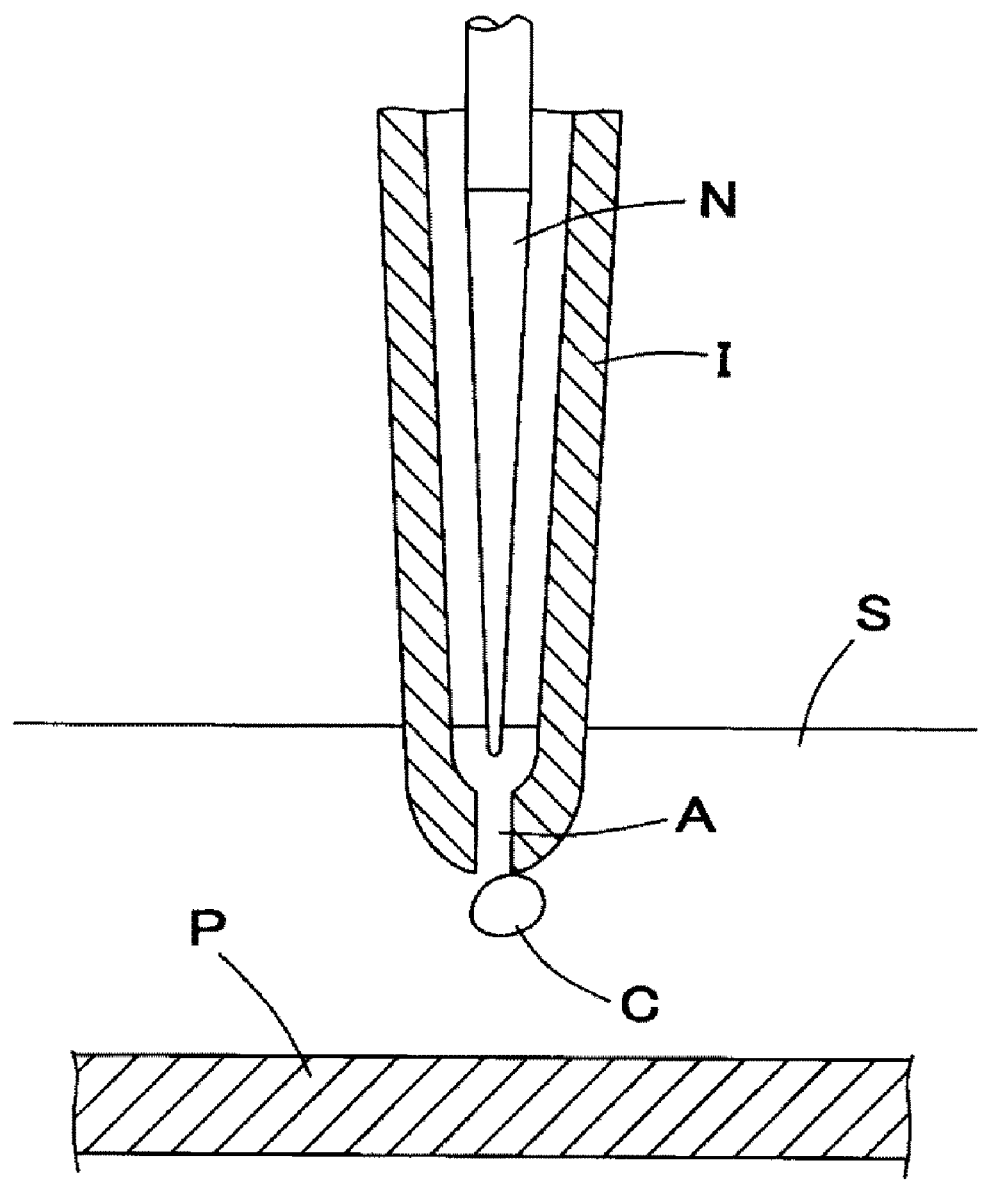
FIG. 13 shows one example of the cell manipulation device utilizing the dielectrophoresis in the prior art.
Figure 14:
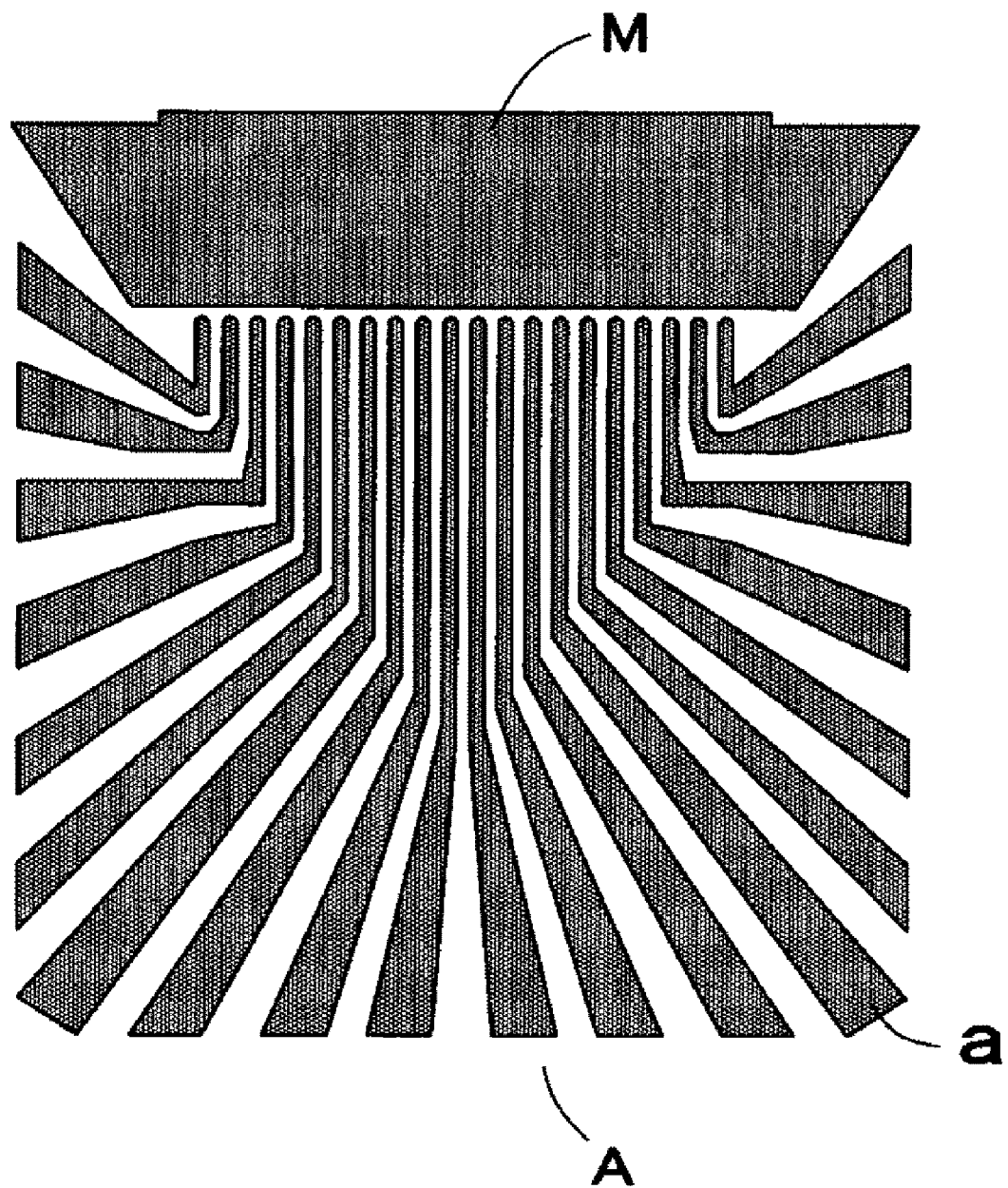
FIG. 14 shows one example of the analysis apparatus for the characteristics of microparticle in the prior art.

FIG. 12 shows a diagrammatic graph of the time-series data of the impedance obtained by the analyzing apparatus (10) shown in FIG. 11. In the graph of FIG. 12, the vertical axis shows the impedance amplitude, and the horizontal axis shows the time.

Significant change in the impedance is observed between when the cell (7) stops on (attaches to) the needle electrodes (5) (see FIG. 6) and when it is away from the needle electrodes (5) (see FIG. 5) because of big change in the real part and imaginary part of the impedance. This results in the significant differences in the measured impedances between these states. In the example shown in FIG. 12, the measured impedance increases when the cell (7) stops on the needle electrodes (5), and it decreases when the cell (7) is away from the needle electrodes (5).

When the analyzing apparatus (1) shown in FIG. 1 is used, the stagnant time τ of the cell (7) in the needle electrodes (5) is determined by the user based on the image obtained by the observation device (3). On the other hand, when the analyzing apparatus (10) shown in FIG. 11 is used, the stagnant time "τ" of the cell (7) is mathematically and physically determined based on the measured impedance amplitude or the change in the impedance amplitude. For example, the input device such as a keyboard electrically connected to the analyzer (4) is used to input and store an upper threshold (a threshold for the impedance increase) and a lower threshold (a threshold for the impedance decrease) corresponding to a change rate of the impedance amplitude into the analyzer (4). Then, the math function of the processing unit comprised in the analyzer (4) is used to calculate the time from when the change rate exceeds the upper threshold to when it exceeds the lower threshold. The time period is designated as the stagnant time "τ".

Therefore, when the analyzing apparatus (10) shown in FIG. 11 is used, the stagnant time "τ" can be determined without causing variances between users, and it can be determined with high accuracy.

The present invention is applied to the apparatus or the method capable of efficiently analyzing the characteristics of the particulate for any manipulation such as transfer, fractionation and concentration.

What is claimed is:

1. An apparatus for analyzing characteristics of a particulate comprising:
    a chamber for receiving a suspension containing a particulate;
    a pair of electrodes positioned in said suspension;
    a voltage device for applying a programmed voltage signal comprising an angle-modulated waveform between the electrodes;
    a capturing device for capturing the area containing at least the tip of the electrode;
    a monitor for displaying a video data with said capturing device;
    a processing unit;
    and an input device for inputting an input data into said processing unit,
    wherein said pair of electrodes independently moves each other or moves together in the fluid,
    wherein said monitor displays said video data with a recording time of said capturing device,
    wherein said processing unit calculates a boundary frequency at which a dielectrophoretic force to a particulate is switched from an attractive force to a repulsive force on the basis of the input data through said input device, and
    wherein said input data is a stagnant time during which the particulate stays in the vicinity of one of said electrodes on the basis of the video data of said monitor and the recording time data of the capturing device.

2. The apparatus for analyzing characteristics of a particulate according to claim 1, further comprising a memory device for storing said video data.

3. The apparatus for analyzing characteristics of a particulate according to claim 1, wherein said particulate is an oval sphere.

4. The apparatus for analyzing characteristics of a particulate according to claim 1, wherein said particulate is hollow.

5. The apparatus for analyzing characteristics of a particulate according to claim 1, wherein said particulate has a complex permittivity different from the fluid surrounding said particulate.

6. The apparatus for analyzing characteristics of a particulate according to claim 1, wherein said particulate has a different frequency spectrum of complex permittivity from the fluid surrounding said particulate.

7. The apparatus for analyzing characteristics of a particulate according to claim 1, wherein said angle-modulated waveform is a frequency-modulated waveform.

8. The apparatus for analyzing characteristics of a particulate according to claim 1, wherein said angle-modulated waveform is a phase modulated waveform.

9. The apparatus for analyzing characteristics of a particulate according to claim 1, wherein said programmed voltage signal has an instantaneous frequency of 1 Hz to 10 GHz.

10. The apparatus for analyzing characteristics of a particulate according to claim 1, wherein said programmed voltage signal has a modulating frequency of 100 kHz or less.

11. The apparatus for analyzing characteristics of a particulate according to claim 1, wherein said electrodes comprises a protrusion.

12. The apparatus for analyzing characteristics of a particulate according to claim 1, wherein said electrodes is in almost V-shaped arrangement.

13. The apparatus for analyzing characteristics of a particulate according to claim 1, wherein at least one of said electrodes moves independently from a container receiving the fluid surrounding said particulate or moves together with said container.

14. The apparatus for analyzing characteristics of a particulate according to claim 13, wherein at least one of said electrodes moves in the same direction as the movement of the container receiving the fluid surrounding said particulate.

15. The apparatus for analyzing characteristics of a particulate according to claim 13, wherein at least one of said electrodes moves in the different direction from the movement of the container receiving the fluid surrounding said particulate.

16. The apparatus for analyzing characteristics of a particulate according to claim 1, wherein at least one of said electrodes moves together with the container receiving the fluid surrounding said particulate.

17. The apparatus for analyzing characteristics of a particulate according to claim 1, wherein said device for applying a programmed voltage signal between the electrodes comprises a waveform generator.

18. The apparatus for analyzing characteristics of a particulate according to claim 1, wherein said device for applying a programmed voltage signal between the electrodes comprises a frequency modulator.

19. The apparatus for analyzing characteristics of a particulate according to claim 1, wherein said device for applying a programmed voltage signal between the electrodes comprises a voltage amplifier.

20. The apparatus for analyzing characteristics of a particulate according to claim 1, wherein said device for applying a programmed voltage signal between the electrodes is capable of applying a DC voltage there between.

21. A method for analyzing characteristics of a particulate, comprising:
    selecting at least one particulate in a fluid;
    positioning said selected particulate in the vicinity of a pair of electrodes;
    applying a programmed voltage signal comprising an angle-modulated waveform for generating a spatially inhomogeneous electric field between said pair of electrodes;
    detecting the movement of the particulate while applying said programmed voltage signal to create a time-series data corresponding to said movement of the particulate; and
    analyzing the characteristics of said particulate based on said time-series data,
    wherein said time-series data is a video data by capturing said movement of the particulate,
    wherein said video data further comprises a recording time data indicating capturing period,
    wherein said step of analyzing the characteristics of the particulate includes:
    displaying said video data with said recording time data in a monitor;
    determining a stagnant time during which the selected particulate stays in the vicinity of one of said electrodes on the basis of said video data displayed in said monitor; and
    calculating on the basis of the determined time a boundary frequency at which a dielectrophoretic force to said selected particulate is switched from an attractive force to a repulsive force.

22. The method for analyzing characteristics of a particulate according to claim 21, wherein said step of detecting the movement of the particulate includes storing said video data with said recording time data in a memory device.

23. The method for analyzing characteristics of a particulate according to claim 21, wherein said particulate is an oval sphere.

24. The method for analyzing characteristics of a particulate according to claim 21, wherein said particulate is hollow.

25. The method for analyzing characteristics of a particulate according to claim 21, wherein said particulate has a complex permittivity different from the fluid surrounding said particulate.

26. The method for analyzing characteristics of a particulate according to claim 21, wherein said particulate has a different frequency spectrum of complex permittivity from the fluid surrounding said particulate.

27. The method for analyzing characteristics of a particulate according to claim 21, wherein said angle-modulated waveform is a frequency-modulated waveform.

28. The method for analyzing characteristics of a particulate according to claim 21, wherein said angle-modulated waveform is a phase modulated waveform.

29. The method for analyzing characteristics of a particulate according to claim 21, wherein said programmed voltage signal has an instantaneous frequency of 1 Hz to 10 GHz.

30. The method for analyzing characteristics of a particulate according to claim 21, wherein said programmed voltage signal has a modulating frequency of 100 kHz or less.

31. The method for analyzing characteristics of a particulate according to claim 21, wherein said pair of electrodes comprises a protrusion.

32. The method for analyzing characteristics of a particulate according to claim 21, wherein said pair of electrodes is in almost V-shaped arrangement.

33. The method for analyzing characteristics of a particulate according to claim 21, wherein said pair of electrodes independently moves each other or moves together in the fluid.

34. The method for analyzing characteristics of a particulate according to claim 21, wherein at least one of said electrodes moves independently from a container receiving the fluid surrounding said particulate or moves together with said container.

35. The method for analyzing characteristics of a particulate according to claim 34, wherein at least one of said electrodes moves in the same direction as the movement of the container receiving the fluid surrounding said particulate.

36. The method for analyzing characteristics of a particulate according to claim 34, wherein at least one of said electrodes moves in the different direction from the movement of the container receiving the fluid surrounding said particulate.

37. The method for analyzing characteristics of a particulate according to claim 21, wherein at least one of said electrodes moves together with the container receiving the fluid surrounding said particulate.

38. The method for analyzing characteristics of a particulate according to claim 21, including: moving said pair of electrodes after analyzing the characteristics of the particulate.

39. The method for analyzing characteristics of a particulate according to claim 21, including: providing a voltage between said electrodes after analyzing the characteristics of the particulate.

40. The method for analyzing characteristics of a particulate according to claim 21, including: gathering said selected particulate after analyzing the characteristics of the particulate.

* * * * *